United States Patent [19]

Kleemann et al.

[11] Patent Number: 4,486,600
[45] Date of Patent: Dec. 4, 1984

[54] PROCESS FOR THE PRODUCTION OF β-HYDROXY-α-AMINOCARBOXYLIC ACIDS

[75] Inventors: Axel Kleemann, Hanau; Bernd Lehmann, Konstanz; Klaus Deller, Hainburg, all of Fed. Rep. of Germany

[73] Assignee: Degussa Aktiengesellschaft, Frankfurt, Fed. Rep. of Germany

[21] Appl. No.: 552,102

[22] Filed: Nov. 16, 1983

[30] Foreign Application Priority Data

Nov. 19, 1982 [DE] Fed. Rep. of Germany ....... 3242748

[51] Int. Cl.³ ........................................... C07C 101/30
[52] U.S. Cl. .................................. 562/567; 562/570; 568/489
[58] Field of Search ................ 562/567, 570; 568/489, 568/491

[56] References Cited

PUBLICATIONS

Weygand, "Preparative Organic Chemistry," pp. 346–347, (1972).

"The Merck Index," pp. ONR-15, ONR-85 and ONR-86, (1976), 9th Ed.

*Primary Examiner*—Michael L. Shippen
*Attorney, Agent, or Firm*—Cushman, Darby & Cushman

[57] ABSTRACT

β-hydroxy-α-aminocarboxylic acids of the formula:

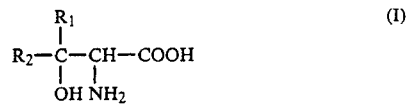

where $R_1$ and $R_2$ are hydrogen or an alkyl group having 1 to 10 carbon atoms are produced by hydrogenating the correspondingly substituted cyanohydrin in a water containing medium first in the presence of a hydrogenation catalyst and an acid at a temperature between $-10°$ and $+40°$ C. and a hydrogen pressure of less than 10 bar, until per mole of cyanohydrogen employed one mole of hydrogen is taken up and then employing the solution obtained as starting material for a Strecker or Bucherer synthesis of an amino acid.

24 Claims, No Drawings

PROCESS FOR THE PRODUCTION OF β-HYDROXY-α-AMINOCARBOXYLIC ACIDS

BACKGROUND OF THE INVENTION

The invention is directed to a process for the production of β-hydroxy-α-aminocarboxylic acids of the general formula:

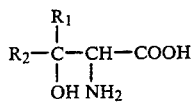

in which $R_1$ and $R_2$ are the same or different and in each case is hydrogen or a straight or branched chain alkyl group having 1 to 10 carbon atoms.

From German OS No. 2515622, the entire disclosure of which is hereby incorporated by reference and relied upon, there is known a process for the production of β-hydroxy-α-aminocarboxylic acids from alkali-sensitive precursors of β-hydroxy aldehydes with the help of the Strecker reaction or in a given case, the modified Strecker reaction. As alkali sensitive precursors of the β-hydroxy aldehyde there serve thereby unsubstituted or substituted vinyl acetate epoxide, 2,5-diacetoxy dioxane, 2,5-dichlorodioxane, monoacetoxyethylene carbonate, monochloroethylene carbonate, vinylene carbonate, monochloroethylene oxide, monoacetoxy acetaldehyde or 2,2-diacetoxy ethanol. However, at least in part, these starting materials are only obtainable with difficulty.

SUMMARY OF THE INVENTION

The invention is directed to a process of preparing compounds of formula (I) by hydrogenating a cyanohydrin of the general formula

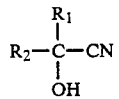

where $R_1$ and $R_2$ are as defined above in an aqueous medium which per mole of cyanohydrin of formula (II) employed contains at least 1 mole of water; in the presence of a palladium or platinum catalyst and, based on the cyanohydrin of general formula (II) at least one equivalent of an inorganic or organic acid or at least one equivalent of an acid ion exchanger, e.g. an acid ion exchange resin, or in the presence of metallic nickel and, again based on the cyanohydrin of general formula (II), at least one equivalent of an acid ion exchanger at a temperature between −10° and +40° C. and a hydrogen pressure of less than 10 bar until one mole of hydrogen is taken up per mole of cyanohydrin of general formula (II) employed, the catalyst and in a given case, the ion exchanger separated off and the remaining solution employed as the starting material for an aminoacid synthesis according to Strecker or Bucherer.

The cyanohydrins of general formula (II) serving as starting materials for the process of the invention can be produced in the simplest manner according to known methods (see, e.g. Houben-Weyl, Methoden der organischen Chemie, 4th edition, Georg Thieme Verlag, Stuttgart, Volume VIII, pages 274 to 278) from the corresponding aldehydes or ketones by reaction with hydrocyanic acid. Insofar as the production of the cyanohydrin is carried out in aqueous solutions, these aqueous solutions can be employed directly for the process of the invention.

The aldehydes or ketones needed for the production of the cyanohydrins of general formula II for their part can, if necessary, also be produced in known manner (see, e.g. Houben-Weyl, Methoden der organischen Chemie, 4th edition, Georg Thieme Verlag, Stuttgart, Volume VII/1, pages 13 to 503 or Volume VII/2a-c).

Examples of cyanohydrins of general formula II reacted according to the process of the invention include propionaldehyde cyanohydrin, butyraldehyde cyanohydrin, isobutyraldehyde cyanohydrin, valeraldehyde cyanohydrin, hexanal cyanohydrin, heptanalcyanohydrin, octanal cyanohydrin, butanone cyanohydrin, pentanone cyanohydrin, methylisopropylketone cyanohydrin, or diisopropylketone cyanohydrin. Also there can be used for example, decanal cyanohydrin, undecanal cyanohydrin, dodecanal cyanohydrin, ethyl isopropyl ketone cyanohydrin.

The process of the invention is especially suited for the reaction of glycolonitrile to form D,L-serine or lactic acid nitrile to form D,L-threonine. There also can be prepared for example β-hydroxy-α-aminohexanoic acid, β-hydroxy-α-aminodecanoic acid, β-hydroxy-α-aminododecanoic acid, β-hydroxy-β-methyl-α-aminopropionic acid, β-hydroxy-β-isopropyl-α-aminopropionic acid, or the β-hydroxy-α-aminocarboxylic acids corresponding to any of the above-mentioned cyanohydrins.

The cyanohydrins of general formula (II) are hydrogenated in a water containing medium which must contain at least 1 mole of water per mole of cyanohydrin employed. Insofar as the solubility of the cyanohydrin employed permits, water can be used as the sole solvent, otherwise there can also be employed as solvents mixtures of water with water soluble alcohols such as methanol, ethanol, n-propanol, isopropyl alcohol, n-butanol, isobutyl alcohol, secondary or tertiary butyl alcohol, dioxane or tetrahydrofuran. The solvent for example can be used in an amount between 0.5 and 100 ml, preferably between 1 and 50 ml, per gram of cyanohydrin employed.

The hydrogenation takes place in the presence of a palladium or platinum catalyst or in the presence of metallic nickel. Suitable catalysts for example are metallic palladium, especially as palladium black, metallic platinum, especially as platinum black, or platinum-IV-oxide. If metallic palladium or platinum is used then it can be employed in the free form as well as in the form of a catalyst on carrier using as the carrier for example, activated carbon, barium sulfate, aluminum oxide, or silica. Especially preferred catalysts are palladium black or palladium on activated carbon. The metallic nickel is preferably employed in the activated form of Raney-nickel. There can also be employed mixtures of several catalysts. The amount of catalyst employed is not critical, to obtain short reaction times, however, it is recommended to use the catalyst, calculated as active metal, in an amount between 0.1 and 100, preferably between 1 and 10 weight percent, based on the cyanohydrin of general formula (II).

In the hydrogenation furthermore, an acid is necessary. In using a palladium or platinum catalyst this can be an organic acid such as for example formic acid, acetic acid, or oxalic acid. However, there are preferably used mineral acids such as sulfuric acid, phosphoric acid and especially hydrochloric acid or an acid ion exchanger, e.g. an ion exchange resin such as a sulfonated styrene-divinyl benzene copolymer. The organic or inorganic acid is employed in the stoichiometric amount of one equivalent, based on the cyanohydrin employed of general formula (II). The use of an excess of acid is unsuitable. The acid ion exchanger must be employed in an amount of at least one equivalent based on the cyanohydrin employed of general formula (II). In this case, however, an excess is not disturbing. If nickel is used as the hydrogenation catalyst there is employed as the acid an acid ion exchanger in an amount of likewise at least one equivalent, based on the cyanohydrin employed of general formula (II).

The hydrogenation is carried out at a temperature between $-10°$ and $+40°$ C., preferably between 0° and 30° C., and a hydrogen pressure of less than 10 bar, preferably between 1 and 2 bar. It is especially advantageous if there is led through the reaction mixture elemental hydrogen. After the taking up of one mole of hydrogen per mole of cyanohydrin of general formula (II) employed, the hydrogenation is ended.

Then the catalyst and in a given case, the ion exchanger is separated off, for example by filtration or centrifugation. The exact composition of the particular solution remaining in each case is not known, however, it contains in solution an α-hydroxy aldehyde of the general formula:

(III)

where $R_1$ and $R_2$ are as defined above. Thus there can be obtained e.g. by means of hydroxylamine hydrochloride the corresponding oxime in nearly theoretical amount, based on the cyanohydrin of general formula (II).

Therefore, this solution can be used directly as the starting material for an aminoacid synthesis according to Strecker of Bucherer. For the synthesis according to Strecker the solution is reacted with hydrocyanic acid or a salt thereof, e.g. sodium cyanide or potassium cyanide, and with ammonia or an ammonium salt, e.g. ammonium chloride, ammonium bromide, or ammonium sulfate, to form the corresponding β-hydroxy-α-aminonitrile and this is subsequently saponified by an acid, e.g. hydrochloric acids or sulfuric acid or basically, e.g. by a base e.g. sodium hydroxide or potassium hydroxide. For the synthesis according to Bucherer the solution is reacted with hydrocyanic acid or a salt thereof and with ammonia and carbon dioxide or with ammonium carbonate and the thereby formed hydantoin substituted in the 5-position is subsequently saponified basically, e.g. with sodium or potassium hydroxide. Then there can be recovered in known manner in each case from the saponification solution the β-hydroxy-α-aminocarboxylic acid, e.g. it can be recovered with the help of an acidic ion exchanger, e.g. a sulfonated styrene-divinyl benzene resin.

The process can comprise, consist essentially of, or consist of the stated steps with the recited materials.

The invention is explained in more detail in the following examples. Unless otherwise indicated all parts and percentages are by weight.

DETAILED DESCRIPTION

EXAMPLE 1

103.6 grams (1 mole) of 55% aqueous glycolonitrile were treated with cooling with 197 grams (1 mole) of 18.5% hydrochloric acid. After addition of 1.14 grams of Pd on activated carbon (10%) hydrogenation was carried out at 6 bar hydrogen pressure under stirring at 25° C. until the take up of 1 mole of hydrogen. Then the catalyst was filtered off.

The filtrate was fed into a solution of 51.2 grams (1.04 moles) of sodium cyanide and 64 grams of ammonia in 210 ml of water at 20° to 25° C.

The mixture was heated to 35° C. and stirred for 3 hours at this temperature. Subsequently the excess ammonia was drawn off in a vacuum. The residue was treated with 493 grams (5 moles) of concentrated hydrochloric acid and heated for 4 hours at boiling.

A serine yield of 82.2 grams (78% of theory) was quantitatively determined by ion exchange chromotography in an aminoacid analyzer.

The D,L-serine could be isolated, e.g. with the help of an acid ion exchanger.

EXAMPLE 2

The procedure was as in Example 1 with the difference that in place of Pd on activated carbon there was employed 1.14 grams of Pd black.

The yield of serine was 84 grams (80% of theory).

EXAMPLE 3

The procedure was as in Example 2 except that the hydrogenation was carried out at normal pressure.

The yield of serine was 82 grams (78% of theory).

EXAMPLE 4

The procedure was as in Example 1 with the difference that in place of Pd on activated carbon there was employed 1.14 grams of metallic platinum.

The yield of serine was 79.5 grams (76% of theory).

EXAMPLE 5

The procedure was as in Example 1 with the difference that in place of palladium on activated carbon there were employed 1.14 grams of Pd on BaSO$_4$(10%).

The yield of serine was 83 grams (79% of theory).

EXAMPLE 6

The procedure was as in Example 1 with the difference that in place of glycolonitrile there was employed a solution of 71 grams (1 mole) of lactic acid nitrile in 58 grams of water. Through ion exchange chromatography in an aminoacid analyzer there was quantitatively determined a threonine yield of 83 grams (70% of theory).

EXAMPLE 7

The procedure was as in Example 1 with the difference that in place of glycolonitrile there was employed a solution of 85 grams of acetone cyanohydrin in 80 grams of water.

There was determined a yield of 90 grams (68% of theory) of β-hydroxyvaline.

EXAMPLE 8

18.7 grams (0.18 mole) of 55% aqueous glycolonitrile and 90 ml of water were treated with 30 ml of an acid ion exchanger (Lewatit S100, sulfonated styrene-divinyl benzene) and 1.2 grams of Pd on activated carbon (10%) and hydrogenated at 25° C. under normal pressure with hydrogen gas until there was taken up 0.18 mole of hydrogen. After filtering off the catalyst and ion exchanger the solution obtained was concentrated in a vacuum until it was half the volume. This concentrate was dosed into a solution of 9.3 grams (0.19 mole) of sodium cyanide, 10.2 grams of ammonium chloride and 12 grams of ammonia in 40 ml of water. The mixture was heated to 35° C. and stirred for 3 hours at this temperature. Subsequently the excess ammonia was drawn off in a vacuum. The residue was treated with 94 grams (0.9 mole) of concentrated hydrochloric acid and heated for 4 hours at the boiling point. The yield of D,L-serine was 14.3 grams (76% of theory).

EXAMPLE 9

The procedure was as in Example 8 but in place of palladium on activated carbon there were employed 2.2 grams of Raney-nickel as catalyst.

The yield of D,L-serine was 14.1 grams (75% of theory).

What is claimed is:

1. A process for the production of β-hydroxy-α-aminocarboxylic acid of the formula:

in which $R_1$ and $R_2$ are hydrogen or an alkyl group having 1 to 10 carbon atoms, comprising hydrogenating a cyanohydrin of the formula:

in an aqueous medium which per mole of cyanohydrin of formula (II) employed contains at least 1 mole of water in the presence of a palladium or platinum catalyst and, based on the cyanohydrin of formula (II) at least one equivalent of an inorganic or organic acid or at least one equivalent of an acid ion exchanger or in the presence of metallic nickel and, again based on the cyanohydrin of formula (II), at least one equivalent of an acid ion exchanger at a temperature between −10° and +40° C. and a hydrogen pressure of less than 10 bar until one mole of hydrogen is taken up per mole of cyanohydrin of formula (II) employed, separating off the catalyst and the ion exchanger if present, and employing the remaining solution as the starting material in the Strecker synthesis of the aminocarboxylic acid by reacting said solution with hydrocyanic acid or a salt thereof and ammonia or ammonium salt to form the corresponding β-hydroxy-2-aminonitrile and saponifying the β-hydroxy-2-aminonitrile with acid or base.

2. A process according to claim 1 wherein the cyanohydrin is glycolonitrile, lactic acid nitrile or acetone cyanohydrin.

3. A process according to claim 1 wherein the hydrogenation is carried out in the presence of a palladium or platinum catalyst and hydrochloric acid.

4. A process according to claim 3 wherein the hydrogenation is carried out at a temperature between 0° and 30° C.

5. A process according to claim 1 wherein the hydrogenation is carried out at a temperature between 0° and 30° C.

6. A process according to claim 5 wherein the hydrogenation is carried out at a hydrogen pressure between 1 and 2 bar.

7. A process according to claim 4 wherein the hydrogenation is carried out at a hydrogen pressure between 1 and 2 bar.

8. A process according to claim 3 wherein the hydrogenation is carried out at a hydrogen pressure between 1 and 2 bar.

9. A process according to claim 1 wherein the hydrogenation is carried out at a hydrogen pressure between 1 and 2 bar.

10. A process according to claim 1 wherein the hydrogenation is carried out in water or a mixture of water and a water soluble alcohol, dioxane or tetrahydrofurane.

11. A process according to claim 1 wherein the aminocarboxylic acid is formed by reacting said remaining solution with an aqueous solution of an alkali metal cyanide and ammonia or an ammonium salt to form the corresponding β-hydroxy-2-aminonitrile and saponifying the β-hydroxy-2-aminonitrile with acid or base.

12. A process according to claim 11 wherein the alkali metal cyanide is sodium cyanide.

13. A process for the production of β-hydroxy-α-aminocarboxylic acid of the formula:

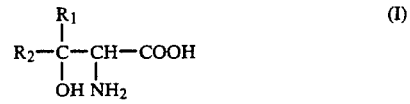

in which $R_1$ and $R_2$ are hydrogen or an alkyl group having 1 to 10 carbon atoms, comprising hydrogenating a cyanohydrin of the formula:

in an aqueous medium which per mole of cyanohydrin of formula (II) employed contains at least 1 mole of water in the presence of a palladium or platinum catalyst and, based on the cyanohydrin of formula (II) at least one equivalent of an inorganic or organic acid or at least one equivalent of an acid ion exchanger or in the presence of metallic nickel and, again based on the cyanohydrin of formula (II), at least one equivalent of an acid ion exchanger at a temperature between −10° and +40° C. and a hydrogen pressure of less than 10 bar until one mole of hydrogen is taken up per mole of cyanohydrin of formula (II) employed, separating off the catalyst and the ion exchanger if present, and employing the remaining solution as the starting material in the Bucherer synthesis of the aminocarboxylic acid by reacting said solution with hydrocyanic acid or a salt thereof and with ammonia and carbon dioxide or with ammonium carbonate to form a 5-substituted hydantoin and saponifying the hydantoin with a base.

14. A process according to claim 13 wherein the cyanohydrin is glycolonitrile, lactic acid nitrile or acetone cyanohydrin.

15. A process according to claim 13 wherein the hydrogenation is carried out in the presence of a palladium or platinum catalyst and hydrochloric acid.

16. A process according to claim 15 wherein the hydrogenation is carried out at a temperature between 0° and 30° C.

17. A process according to claim 13 wherein the hydrogenation is carried out at a temperature between 0° and 30° C.

18. A process according to claim 17 wherein the hydrogenation is carried out at a hydrogen pressure between 1 and 2 bar.

19. A process according to claim 16 wherein the hydrogenation is carried out at a hydrogen pressure between 1 and 2 bar.

20. A process according to claim 15 wherein the hydrogenation is carried out at a hydrogen pressure between 1 and 2 bar.

21. A process according to claim 13 wherein the hydrogenation is carried out at a hydrogen pressure between 1 and 2 bar.

22. A process according to claim 13 wherein the hydrogenation is carried out in water or a mixture of water and a water soluble alcohol, dioxane or tetrahydrofurane.

23. A process according to claim 13 wherein there is employed alkali metal cyanide.

24. A process according to claim 23 wherein there is employed alkali metal cyanide is sodium cyanide.

* * * * *